US00PP24374P2

(12) United States Plant Patent
Marczyński

(10) Patent No.: US PP24,374 P2
(45) Date of Patent: Apr. 8, 2014

(54) ***CLEMATIS* PLANT NAMED 'KRAKOWIAK'**

(50) Latin Name: *Clematis viticella*
Varietal Denomination: Krakowiak

(75) Inventor: Szczepan Marczyński, Pruszków (PL)

(73) Assignee: Spring Meadow Nursery Inc., Grand Haven, MI (US)

( * ) Notice: Subject to any disclaimer, the term of this patent is extended or adjusted under 35 U.S.C. 154(b) by 146 days.

(21) Appl. No.: 13/506,084

(22) Filed: Mar. 24, 2012

(51) Int. Cl.
*A01H 5/00* (2006.01)

(52) U.S. Cl.
USPC ..... Plt./228

(58) Field of Classification Search
USPC ..... Plt./228
See application file for complete search history.

(56) References Cited

PUBLICATIONS

UPOV PLUTO 201303 CA Citation for 'Krakowiak' Oct. 31, 2012.*
UPOV PLUTO 201303 PL Citation for 'Krakowiak' Jan. 15, 2010.*
UPOV PLUTO 201303 QZ Citation for 'Krakowiak' Apr. 15, 2011.*

* cited by examiner

*Primary Examiner* — Wendy C Haas
(74) *Attorney, Agent, or Firm* — C. A. Whealy

(57) ABSTRACT

A new and distinct cultivar of *Clematis* plant named 'Krakowiak' characterized by its upright and vining plant habit; relatively small leaves; freely flowering habit; long flowering period; and single light red purple-colored flowers with broad darker red purple-colored central stripes.

2 Drawing Sheets

Botanical designation: *Clematis viticella.*
Cultivar denomination: 'KRAKOWIAK'.

BACKGROUND OF THE INVENTION

The present invention relates to a new and distinct cultivar of *Clematis* plant, botanically known as *Clematis viticella* and hereinafter referred to by the name 'Krakowiak'.

The new *Clematis* plant is a product of a planned breeding program conducted by the Inventor in Pruszków, Poland. The objective of the breeding program is to create new *Clematis* plants with brightly-colored flowers.

The new *Clematis* plant originated from an open-pollination in 2000 in Pruszków, Poland of an unidentified selection of *Clematis viticella*, not patented, as the female, or seed parent with an unknown selection of *Clematis viticella*, not patented, as the male, or pollen, parent. The new *Clematis* plant was discovered and selected by the Inventor as a single flowering plant from within the progeny of the stated open-pollination in a controlled environment in Pruszków, Poland in 2000.

Asexual reproduction of the new *Clematis* plant by cuttings in Pruszków, Poland since June, 2004 has shown that the unique features of this new *Clematis* plant are stable and reproduced true to type in successive generations.

SUMMARY OF THE INVENTION

Plants of the new *Clematis* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Krakowiak'.

These characteristics in combination distinguish 'Krakowiak' as a new and distinct *Clematis* plant:

1. Upright and vining plant habit.
2. Relatively small leaves.
3. Freely flowering habit.
4. Long flowering period.
5. Single light red purple-colored flowers with broad darker red purple-colored central stripes.

Plants of the new *Clematis* differ primarily from plants of the female parent selection primarily in flower color.

Plants of the new *Clematis* can be compared to plants of the *Clematis* 'Abundance', not patented. Plants of the new *Clematis* differ primarily from plants of 'Abundance' in the following characteristics:

1. Plants of the new *Clematis* are more freely flowering than plants of 'Abundance'.
2. Plants of the new *Clematis* flower for a longer period of time than plants of 'Abundance'.
3. Plants of the new *Clematis* and 'Abundance' differ in flower color as plants of 'Abundance' have red purple-colored flowers.

Plants of the new *Clematis* can be compared to plants of the *Clematis* 'Little Nell', not patented. Plants of the new *Clematis* differ primarily from plants of 'Little Nell' in the following characteristics:

1. Plants of the new *Clematis* are more freely flowering than plants of 'Little Nell'.
2. Plants of the new *Clematis* flower for a longer period of time than plants of 'Little Nell'.
3. Plants of the new *Clematis* and 'Little Nell' differ in flower color as plants of 'Little Nell' have light pink-colored flowers.

BRIEF DESCRIPTION OF THE PHOTOGRAPHS

The accompanying colored photographs illustrate the overall appearance of the new *Clematis* plant showing the colors as true as it is reasonably possible to obtain in colored reproductions of this type. Colors in the photographs may differ slightly from the color values cited in the detailed botanical description which accurately describe the actual colors of the new *Clematis* plant.

The photograph on the first sheet comprises a side perspective view of a typical flowering plant of 'Krakowiak' grown in an outdoor nursery.

The photograph on the second sheet is a close-up view of a typical flowering plant of 'Krakowiak'.

DETAILED BOTANICAL DESCRIPTION

Plants used for the aforementioned photographs and following description were grown during the summer in an outdoor nursery in Pruszków, Poland and under cultural practices which closely approximate commercial production. During the production of the plants, day temperatures ranged from 18° C. to 23° C. and night temperatures ranged from 13° C. to 16° C. Plants were three years old when the photographs and the description were taken. In the following description, color references are made to The Royal Horticultural Society Colour Chart, 1995 Edition, except where general terms of ordinary dictionary significance are used.

Botanical classification: *Clematis viticella* 'Krakowiak'.

Parentage:

*Female, or seed, parent.*—Unidentified selection of *Clematis viticella*, not patented.

*Male, or pollen, parent.*—Unknown selection of *Clematis viticella*, not patented.

Propagation:

*Type.*—By cuttings.

*Time to initiate roots, summer.*—About two weeks.

*Time to produce a rooted young plant, summer.*—About one to three months.

*Root description.*—Fine to thick; color, close to 163B.

*Rooting habit.*—Freely branching.

Plant description:

*Plant and growth habit.*—Perennial vine; upright and vining plant habit; vigorous growth habit.

*Plant height.*—About 250 cm to 300 cm.

*Plant width.*—About 120 cm to 150 cm.

*Lateral branch description.*—Branching habit: Freely branching habit, about 16 lateral branches develop per plant. Length: About 40 cm to 50 cm. Diameter: About 2 mm. Internode length: About 10 cm to 20 cm. Texture: Smooth, glabrous. Color, developing: Close to 144B. Color, fully developed: Close to 175A.

Foliage description:

*Arrangement.*—Opposite, bi-pinnately compound with 9 to 15 leaflets.

*Length, leaflet.*—About 2 cm to 6 cm.

*Width, leaflet.*—About 1 cm to 2.5 cm.

*Shape, leaflet.*—Ovate, lobed.

*Apex, leaflet.*—Acute.

*Base, leaflet.*—Truncate.

*Margin, leaflet.*—Entire.

*Texture, leaflet, upper and lower surfaces.*—Smooth, glabrous.

*Venation pattern, leaflet.*—Pinnate.

*Color, leaflet.*—Developing, upper and lower surfaces: Close to 137A. Developing, lower surface: Close to 138A. Fully expanded, upper surface: Close to 139A; venation, close to 139A. Fully expanded, lower surface: Close to 137B; venation, close to 137B.

*Petioles.*—Length, leaflets: About 4 cm to 4.5 cm. Diameter, leaflets: About 1 mm. Color: Developing leaflets, upper and lower surfaces: Close to 146B. Fully expanded leaflets, upper surface: Close to 146A. Fully expanded leaflets, lower surface: Close to 146B. Petioles: Length: About 4 cm to 4.5 cm. Diameter: About 1 mm. Texture, upper and lower surfaces: Smooth, glabrous. Color, upper and lower surfaces: Close to 146B.

Flower description:

*Flower shape, arrangement and flowering habit.*—Single cruciform-shaped terminal and axillary flowers; flowers face outwardly; freely flowering habit, about 650 flowers develop per plant.

*Natural flowering season.*—Continuous flowering from July to September in Poland.

*Flower longevity on the plant.*—About eight to ten days; flowers not persistent.

*Fragrance.*—None detected.

*Flower buds.*—Length: About 1.5 cm to 2 cm. Diameter: About 5 mm to 7 mm. Shape: Narrowly ovate. Color: Close to 145B and 75A.

*Flower diameter.*—About 6 cm to 8 cm.

*Petals.*—None observed.

*Sepals.*—Quantity and arrangement: Four in a single whorl. Length: About 3 cm to 3.5 cm. Width: About 1.5 cm to 2 cm. Shape: Obovate to oblanceolate; recurved. Apex: Apiculate. Base: Narrowly cuneate. Margin: Entire, irregularly dentate; undulate. Texture, upper and lower surfaces: Smooth, glabrous. Color: When opening, upper surface: Close to 70B; central stripe, close to 67A. When opening, lower surface: Close to 75A; central stripe, close to 69C. Fully opened, upper surface: Close to 74C; center, close to 57A to 57B. Fully opened, lower surface: Close to 75A; central stripe, close to 67A to 67B.

*Peduncles.*—Length: About 6 cm to 8 cm. Diameter: About 1 mm. Strength: Moderately strong. Texture: Smooth, glabrous. Color: Close to 146B.

*Reproductive organs.*—Stamens: Quantity per flower: About 30. Anther shape: Lanceolate. Pollen color: Close to 145C. Pistils: Quantity per flower: About 35 to 40. Pistil length: About 1 cm. Stigma shape: Conical, narrow. Stigma color: Close to 145C. Ovary color: Close to 143C.

*Seeds.*—Quantity per flower: About 35 to 40.

Disease & pest resistance: Plants of the new *Clematis* have not been noted to be resistant to pathogens and pests common to *Clematis* plants.

Garden performance: Plants of the new *Clematis* have exhibited good tolerance to rain and wind and have been observed to be suitable for USDA Hardiness Zone 5 and USDA Heat Zone 9.

It is claimed:

1. A new and distinct *Clematis* plant named 'Krakowiak' as illustrated and described.

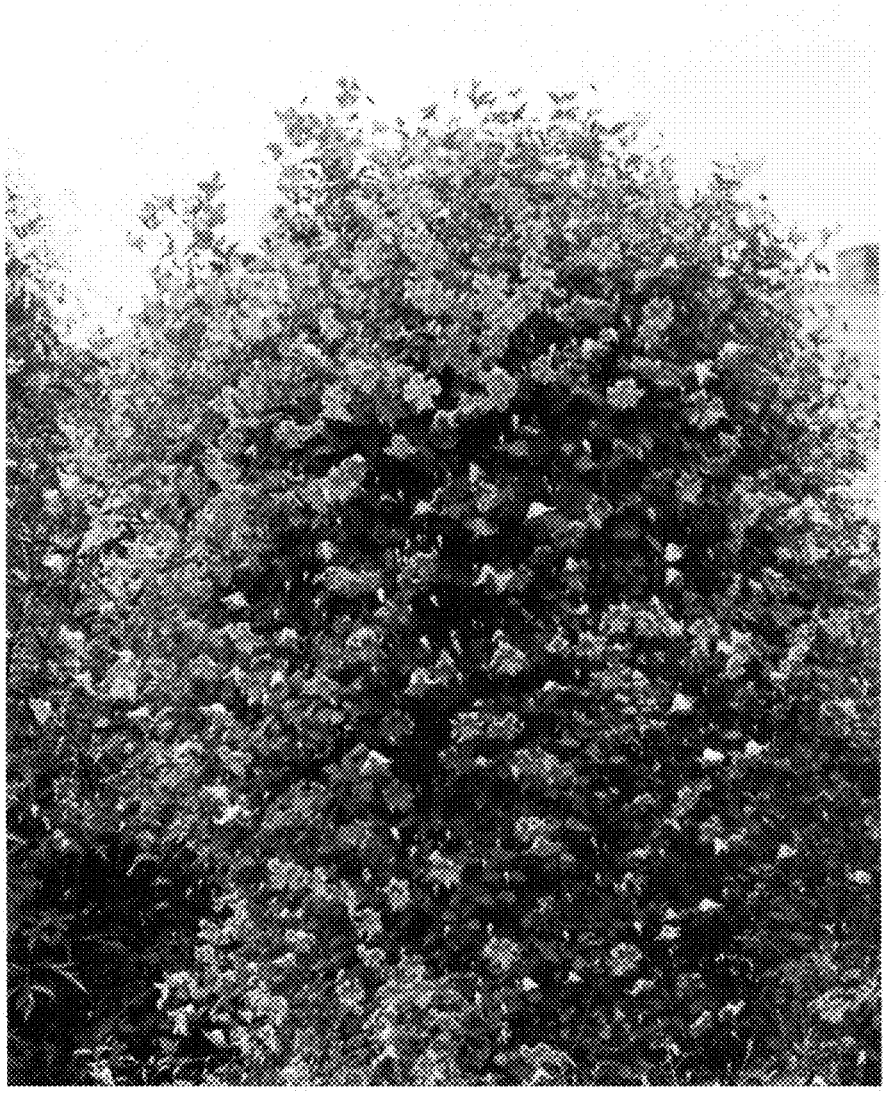

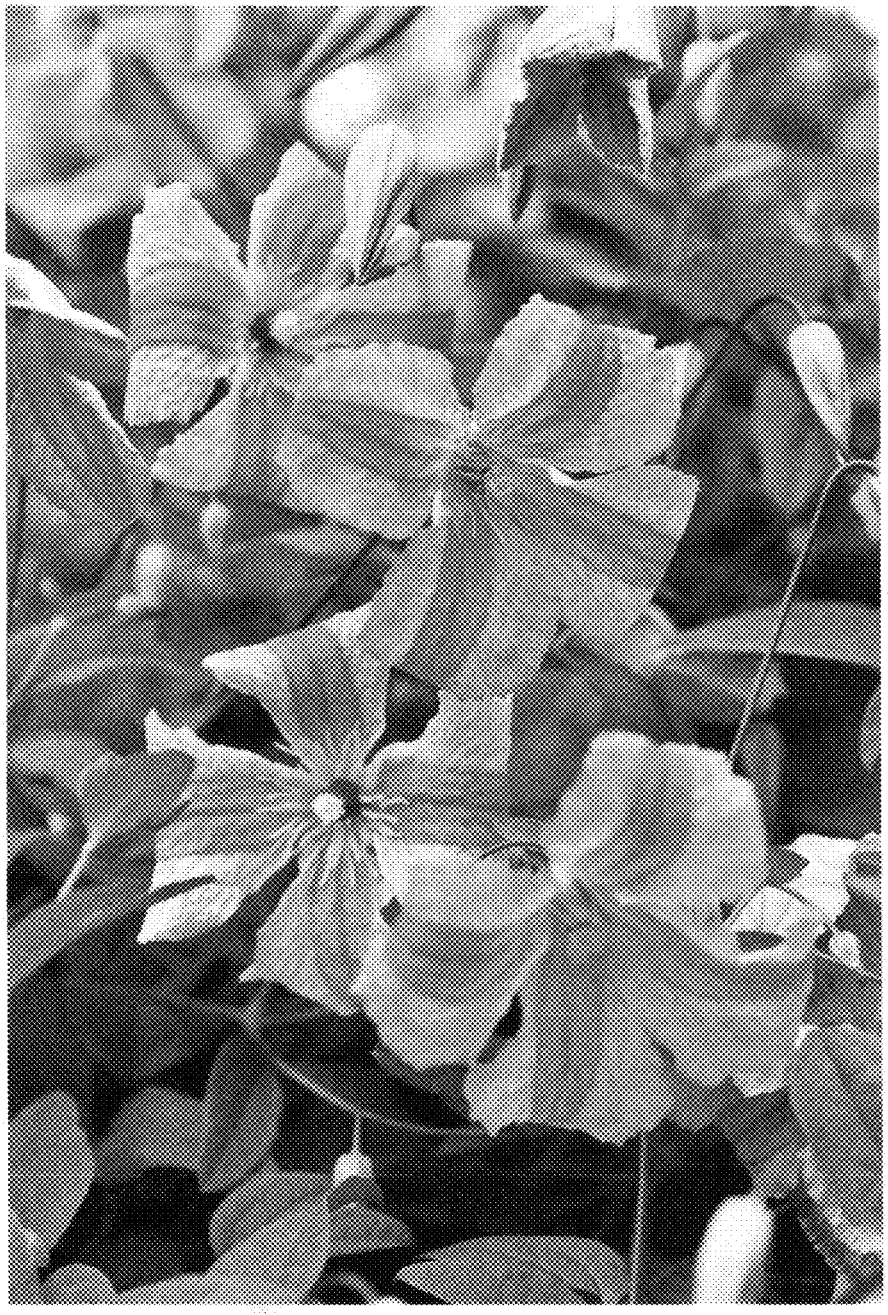

* * * * *